(12) United States Patent
Sobel

(10) Patent No.: US 7,381,056 B2
(45) Date of Patent: Jun. 3, 2008

(54) SUBSTRATE OF POLISHING COMPOUND FOR TEETH AND METHOD

(76) Inventor: Kathleen G. Sobel, 9858 E. Irwin Cir., Mesa, AZ (US) 85208

( * ) Notice: Subject to any disclaimer, the term of this patent is extended or adjusted under 35 U.S.C. 154(b) by 243 days.

(21) Appl. No.: 11/217,975

(22) Filed: Sep. 1, 2005

(65) Prior Publication Data
US 2006/0051724 A1    Mar. 9, 2006

Related U.S. Application Data

(60) Provisional application No. 60/607,169, filed on Sep. 3, 2004.

(51) Int. Cl.
*A61C 15/00* (2006.01)
(52) U.S. Cl. ........................ 433/216; 433/124
(58) Field of Classification Search ............... 433/80, 433/89, 90, 124, 216
See application file for complete search history.

(56) References Cited

U.S. PATENT DOCUMENTS

| | | | |
|---|---|---|---|
| 217,300 A | 7/1879 | Starr | |
| 1,138,479 A | 5/1915 | Hough | |
| 1,512,503 A * | 10/1924 | Semmes, Jr. | 222/549 |
| 4,690,642 A | 9/1987 | Kyotani | 433/142 |
| 4,998,978 A | 3/1991 | Varum | 132/321 |
| 5,836,810 A | 11/1998 | Asum | 451/526 |
| 6,267,594 B1 | 7/2001 | Hugo | 433/199 |
| 6,287,120 B1 * | 9/2001 | Wiesel | 433/215 |
| 6,312,257 B1 | 11/2001 | Aschmann et al. | 433/165 |
| 6,343,932 B1 * | 2/2002 | Wiesel | 433/215 |
| 6,386,874 B2 | 5/2002 | Bachmann et al. | 433/142 |
| 6,506,053 B2 * | 1/2003 | Wiesel | 433/215 |
| 6,508,649 B2 | 1/2003 | Gratz | 433/142 |
| 6,514,484 B2 | 2/2003 | Rajaiah et al. | 424/53 |
| 6,649,147 B1 | 11/2003 | Ye et al. | 424/49 |
| 6,860,738 B2 | 3/2005 | Bachmann et al. | 433/142 |

* cited by examiner

*Primary Examiner*—Ralph A. Lewis
(74) *Attorney, Agent, or Firm*—Cahill, von Hellens & Glazers, PLC

(57) ABSTRACT

A malleable strip of polishing compound is conformable to overlie the occlusal, buccal and lingual surfaces of the maxillary or the mandibular teeth in an oral cavity. After mounting of the strip, a conventional prophy cup attached to a conventional dental hand piece is used to capture the compound adjacent each tooth and to perform a polishing procedure.

1 Claim, 3 Drawing Sheets

SUBSTRATE OF POLISHING COMPOUND FOR TEETH AND METHOD

CROSS REFERENCE TO RELATED APPLICATIONS

The present application is related to and claims priority of a provisional application entitled "MALLEABLE STRIP FOR USE FOR A DENTAL PROPHYLACTIC PROCEDURE", filed Sep. 3, 2004, and assigned Ser. No. 60/607,169, disclosing an invention by the present inventor.

BACKGROUND OF THE INVENTION

1. Field of the Invention

The present invention relates to a polishing compound for the enamel surfaces of teeth and, more particularly, to a malleable substrate of polishing compound for teeth.

2. Description of Related Prior Art

Dental products used in the polishing process of a dental prophylactic procedure have changed dramatically in the past twenty years. In particular, the consistency of the product has changed to produce less splatter upon application of a rotating brush. For the benefit of patients, the palatability of the polishing compound has been enhanced by providing the patient with a choice of flavors.

Many years ago, the polishing compound used by a dentist or hygienist was packaged in a jar and the prophy cup attached to a dental hand piece was dipped into the jar and then the prophy cup was applied to the teeth. With the advent of potentially fatal diseases that may be present in an oral cavity, the use of a common jar as a source of polishing material for multiple patients was no longer medically acceptable. To avoid this potential medical problem, the polishing compound was packaged in small sealed containers with enough polishing compound to polish the teeth of a single patient. After a one time use, such a container was disposed of as waste to prevent the spread of disease to other patients.

For a dentist or hygienist to periodically reload the rotatable prophy cup attached to a conventional dental hand piece multiple times during a polishing procedure is very time consuming. As each procedure performed in a dental office must be efficiently carried out, the cumulative time spent reloading a prophy cup becomes significant and reduces the income per time generated. Moreover, due to inattention or clumsiness, the container may be dropped inadvertently and then must be replaced. Such replacement incurs further wasted time to retrieve a replacement container from a place of storage, open it and return to the patient to continue the polishing procedure.

SUMMARY OF THE INVENTION

The present invention is a malleable strip of polishing compound that is laid upon and formed about a number of adjacent teeth. With such mounting of the strip, the polishing compound is in place at the desired locations. Thereafter, a dentist or a hygienist can use a conventional prophy cup attached to a conventional dental hand piece to engage the polishing compound and perform the polishing procedure. On completion, a conventional nozzle ejecting a stream of water is used to loosen any residual polishing compound and a conventional suction line withdraws the mixture of water and polishing compound.

It is therefore a primary object of the present invention to provide a strip of polishing compound for placement on teeth to be polished.

Another object of the present invention is to provide a malleable strip of polishing compound for placement on and about a series of adjacent teeth.

Still another object of the present invention is to provide a polishing compound ready for use upon mounting a strip of the polishing compound on selected teeth.

Yet another object of the present invention is to eliminate the need for successive reloading with a polishing compound a prophy cup used by dentists and hygienists to polish teeth.

A further object of the present invention is to minimize waste of polishing compound by providing a strip of polishing compound that is laid upon teeth to be polished and which is essentially completely consumed during a polishing procedure.

A still further object of the present invention is to provide a polishing compound in a form requiring little manual dexterity by a dentist or a hygienist.

A yet further object of the present invention is to provide an efficient method for polishing teeth by a dentist or hygienist.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which.

DESCRIPTION OF THE PREFERRED EMBODIMENT

During a prophylaxis treatment by a dentist or a hygienist, the final step is usually a cleaning and polishing procedure using a prophylaxis paste in conjunction with a rotatable prophy cup attached to a conventional dental hand piece.

Figure 1:
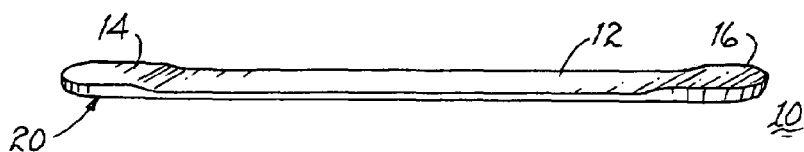
FIG. 1 illustrates a mandibular strip of polishing compound.
Figure 2:
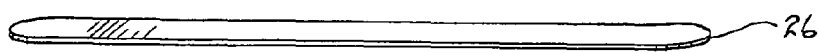
FIG. 2 illustrates a liner disposed between a pair of strips of polishing compound for packaging purposes.

Referring to FIG. 1, there is illustrated a strip 10 of prophylaxis paste. This paste may be of the type sold by Dentsply International, Inc., of York, Pa. under the trademark NUPRO. This paste is a combination of pumice, glycerin, sodium saccharin, water, sodium silicate, flavoring, color, thickeners and preservatives. It is a unique blend of polishing and cleaning agents designed for professional application during a standard practice hygiene procedure. Other commercially available pastes for this purpose may be used as well as a unique blend of ingredients that may be developed for particular purposes.

Figure 4:
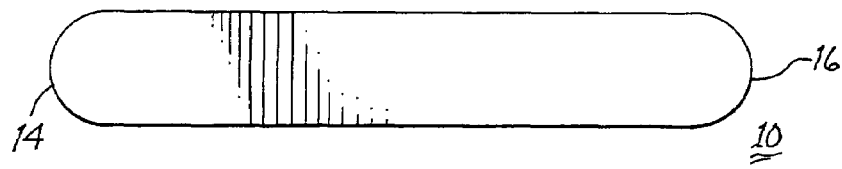
FIG. 4 illustrates a top view of a strip of polishing compound.

As illustrated in FIG. 1, strip 10 may have a relatively thin central section 12 and ends 14, 16 of thicker cross section. A representative plan view of strip 10 is illustrated in FIG. 4. The width and length of the strip will vary as a function of the oral cavity of the patient and may be relatively large, medium, small or child sized (PEDO).

Figure 3:
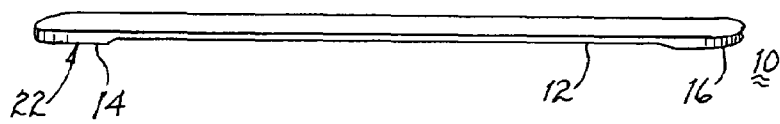
FIG. 3 illustrates a maxillary strip of polishing compound.
Figure 5:
FIG. 5 illustrates a maxillary and mandibular strips of polishing compound separated from one another by a liner.

For reasons that will be described below, strip 10, shown in FIG. 1, may be referred to as a mandibular strip 20. Strip 10, shown in FIG. 3, may be referred to as a maxillary strip 22. The main differences between the mandibular strip and the maxillary strip is that thicker ends 14, 16 of the maxillary strip are oriented downwardly when in use compared to the ends of mandibular strip 20 which are oriented upwardly when in use. For packaging purposes, the mandibular and maxillary strips may be stacked with a release sheet 26 disposed therebetween to permit selective removal of either strip, as shown in FIG. 5. Thereby, the dentist or hygienist would remove either mandibular strip 20 or maxillary strip 22, depending upon whether the lower or upper teeth were to be cleaned and polished first.

Figure 6:
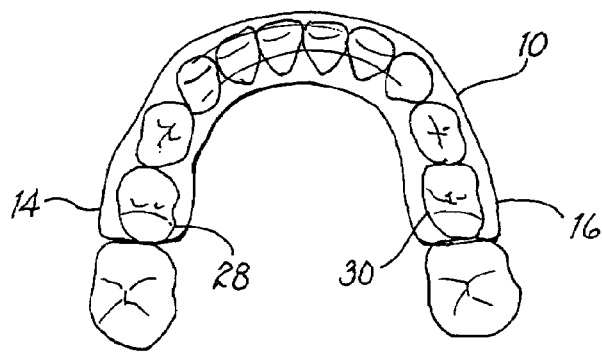
FIG. 6 illustrates a representative set of teeth having a strip of polishing compound formed thereabout.
Figure 7:
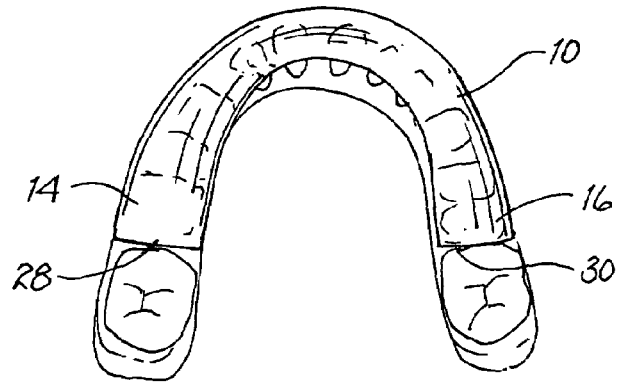
FIG. 7 illustrates a further view of conformance of a strip of polishing compound to a set of teeth.
Figure 8:
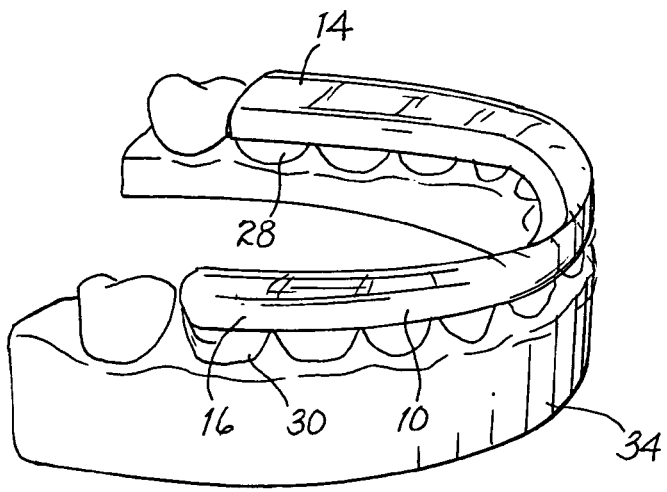
FIG. 8 is a perspective view of a strip of polishing compound formed about a representative set of teeth.
Figure 9:
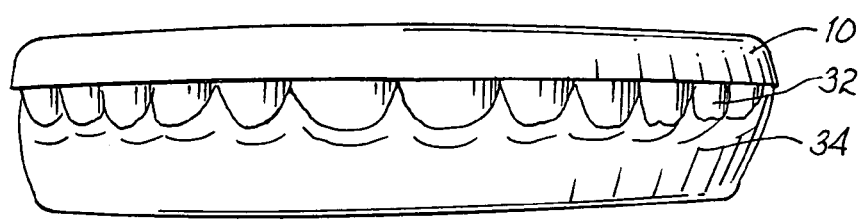
FIG. 9 is a frontal view of a strip of polishing compound formed about a set of teeth.

As shown in FIG. 6, a strip 10 is placed by a dentist or a hygienist upon the occlusal surfaces of the teeth with ends 14, 16 of the strip being placed distal of the second deciduous molars. As shown in further detail in FIGS. 7, 8 and 9, strip 10 is placed upon the occlusal surface of the teeth with the edges molded to be in contact with the lingual and buccal surfaces of teeth 32; it is to be understood that dental mold 34 incorporating teeth 32 are representative of the teeth in an oral cavity. By having strip 10 malleable, it readily conforms with the teeth during the manual process by a dentist or hygienist to mold the edges of strip 10 adjacent the lingual and buccal surfaces. Preferably, the strip is at least slightly translucent to permit viewing by the dentist or hygienist of any inconsistency of a tooth structure.

Figure 10:
FIG. 10 illustrates a further strip of polishing compound.
Figure 11:
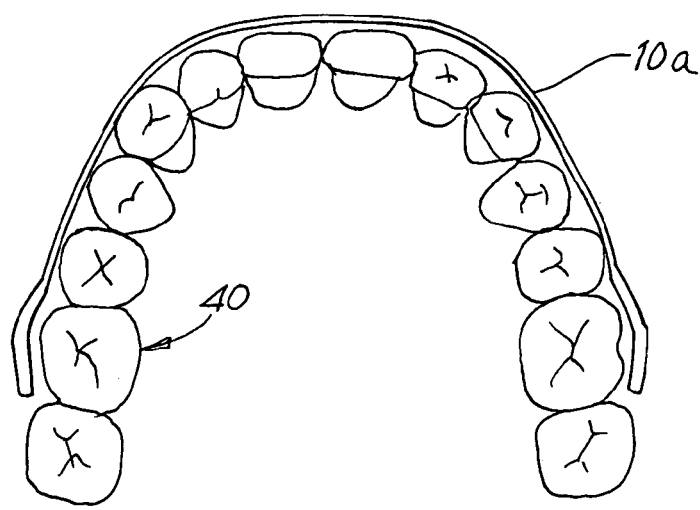
FIG. 11 illustrates a representative set of teeth with the strip shown in FIG. 10 formed about the buccal surfaces of the teeth.
Figure 12:
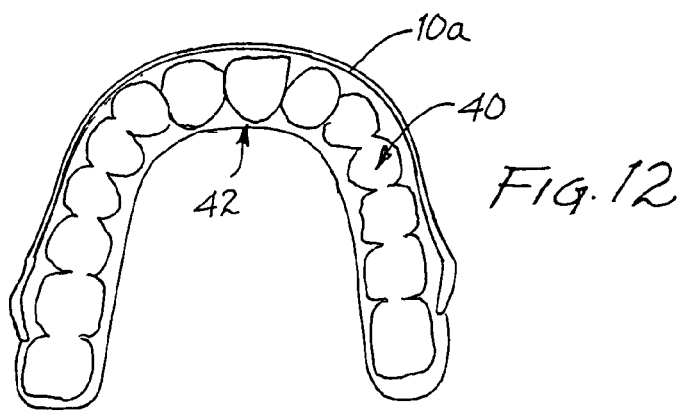
FIG. 12 further illustrates a strip of polishing compound disposed along the buccal surfaces of a set of teeth.

FIG. 10 illustrates a strip 10a having increased thickness ends 14a and 16a particularly adapted for placement along the buccal surfaces of teeth 40, as illustrated in FIG. 11. FIG. 12 illustrates a mold 42 supporting teeth 40 representative of actual teeth present within an oral cavity. Strip 10a is placed along the buccal surfaces of all but the proximal molars, as illustrated.

Figure 13:
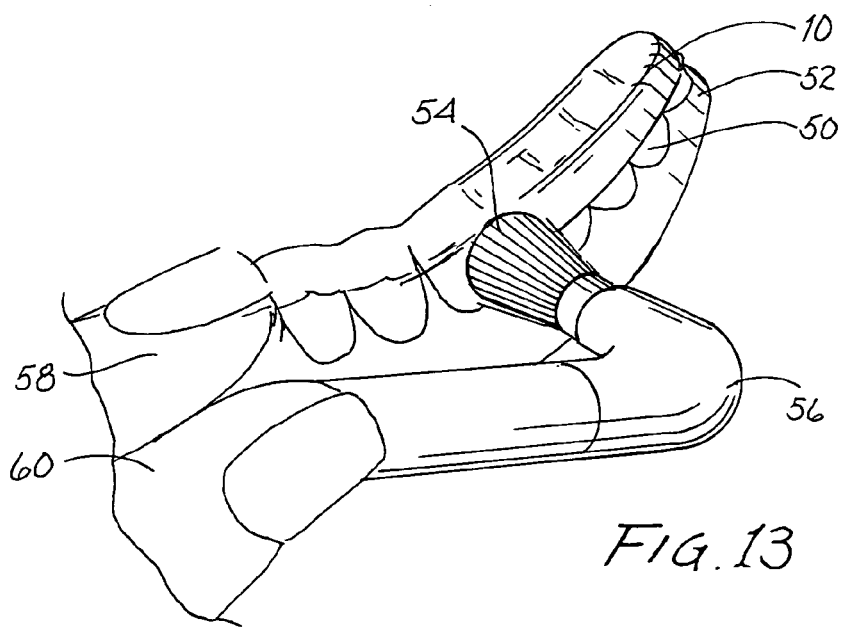
FIG. 13 illustrates the polishing procedure of a set of teeth using the present invention and particularly illustrating removal of the polishing compound as a result of the act of polishing.
Figure 14:
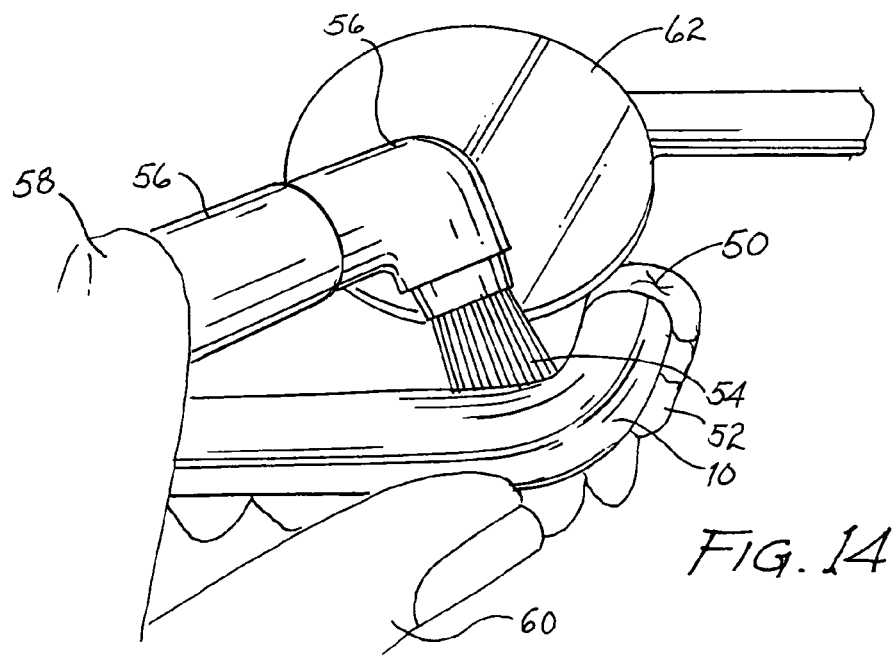
FIG. 14 particularly illustrates polishing the lingual surfaces of a set of teeth along with a dental mirror used therefor by a dentist or hygienist.

FIGS. 13 and 14 are primarily illustrative of the methodology useable by a dentist or hygienist in practicing the present invention. For illustrative purposes, a dental mold 50 supporting a set of teeth 52 will be described. It is to be understood that this mold and teeth are representative of the gum and teeth in an oral cavity. FIG. 13 illustrates the act of cleaning and polishing the buccal surfaces of teeth 50 with a prophy cup 54 rotatably mounted to a conventional dental hand piece 56. Fingers 58, 60 of a dentist or hygienist holding the hand piece are shown. Upon rotation of prophy cup 54, it is passed over strip 10 (or strip 10a) that has been molded to lie adjacent the occlusal, buccal and lingual surfaces of teeth 50. By moving prophy cup 54 across the surfaces of the teeth, it will contact the prophylaxis paste of strip 10 (10a) and swirl to around in the normal manner to effect the cleaning and polishing procedure. As particularly shown in FIG. 13, the buccal surfaces of teeth 50 are being cleaned and polished.

FIG. 14 is similar to FIG. 13 except that it illustrates prophy cup 54 engaging the prophylaxis paste of strip 10 for cleaning and polishing the lingual surfaces of teeth 50. As illustrated, a dental mirror 62 is usually used by a dentist or hygienist to view the cleaning and polishing procedure and to insure that the surfaces of the teeth are being contacted by prophy cup 54.

As discussed above, ends 14 and 16 of strip 10 are placed distal of the respective first molar and thereby provide sufficient material to clean and polish the first molars. The remaining prophylaxis paste attendant ends 14 and 16 is sufficient to polish and clean the adjacent molars. For all proximal teeth, the thickness of the strip provides sufficient prophylaxis paste to permit cleaning of the respective supra gingival surfaces of the underlying teeth.

By using strips 10, the present repetitive filling of the prophy cup from a container of prophylaxis paste is completely avoided. Furthermore, the malleable nature of strip 10 permits it to be easily and quickly formed around the surfaces of a set of teeth being cleaned and sufficient quantity of prophylaxis paste is readily available adjacent each respective tooth without requiring any refilling of the prophy cup.

I claim:

1. A method for polishing a patient's teeth comprising the steps of:
    a) selecting a pre-formed strip of polishing compound having a center section of a first thickness and ends of a second thickness wherein the second thickness is greater than the first thickness, said strip having a removable release sheet along one side;
    b) removing the removable release sheet from said strip;
    c) positioning said strip on the patient's teeth so that it overlays the occlusal, buccal and lingual surfaces of the patient's teeth, wherein said ends of said strip having a second thickness are positioned short of the patient's second molars;
    d) conforming the positioned strip to the patient's teeth;
    e) applying a rotatable prophy cup against the strip to polish each underlying tooth and using extra material in the ends of the strip having a second thickness to polish molars adjacent the patient's first molars; and
    f) consuming the material of the strip while polishing the teeth with the prophy cup.

* * * * *